US012805547B2

(12) United States Patent
Watson et al.

(10) Patent No.: US 12,805,547 B2
(45) Date of Patent: Nov. 24, 2026

(54) COMPOSITIONS CONTAINING LINOLEIC ACID

(71) Applicant: MARS, INCORPORATED, McLean, VA (US)

(72) Inventors: Adrian Watson, Aimargues (FR); David Allaway, Leicestershire (GB); Gaelle Thomas, Leicestershire (GB)

(73) Assignee: MARS, INCORPORATED, McLean, VA (US)

( * ) Notice: Subject to any disclaimer, the term of this patent is extended or adjusted under 35 U.S.C. 154(b) by 847 days.

(21) Appl. No.: 17/274,284

(22) PCT Filed: Sep. 10, 2019

(86) PCT No.: PCT/US2019/050398

§ 371 (c)(1),
(2) Date: Mar. 8, 2021

(87) PCT Pub. No.: WO2020/055856

PCT Pub. Date: Mar. 19, 2020

(65) Prior Publication Data

US 2021/0337830 A1 Nov. 4, 2021

(30) Foreign Application Priority Data

Sep. 10, 2018 (EP) .................................... 18306184

(51) Int. Cl.

| | |
|---|---|
| ***A23K 20/158*** | (2016.01) |
| ***A23K 20/20*** | (2016.01) |
| ***A23K 50/40*** | (2016.01) |
| ***A61K 9/00*** | (2006.01) |
| ***A61K 31/201*** | (2006.01) |
| ***A61K 33/30*** | (2006.01) |

(52) U.S. Cl.

CPC ............ *A23K 20/158* (2016.05); *A23K 20/30* (2016.05); *A23K 50/40* (2016.05); *A61K 9/0053* (2013.01); *A61K 31/201* (2013.01); *A61K 33/30* (2013.01)

(58) Field of Classification Search

CPC ...... A23K 20/158; A23K 20/30; A23K 50/40; A23K 10/20; A61K 9/0053; A61K 31/201; A61K 33/30; A61K 2300/00; A23L 33/12; A23L 33/16; A61P 17/00; A23D 9/00; A23V 2002/00; A23V 2200/318; Y10S 426/805

See application file for complete search history.

(56) References Cited

U.S. PATENT DOCUMENTS

| | | | | |
|---|---|---|---|---|
| 5,200,218 A | 4/1993 | Lasater et al. | | |
| 5,792,449 A | 8/1998 | Bryce-Smith | | |
| 6,177,107 B1 * | 1/2001 | Watson | A23K 50/48 | 514/351 |
| 6,331,567 B1 | 12/2001 | Watson et al. | | |
| 7,297,677 B2 * | 11/2007 | Fray | A61P 17/00 | 514/20.7 |
| 7,479,286 B2 | 1/2009 | Couzy et al. | | |
| 9,884,035 B2 | 2/2018 | Brockman et al. | | |
| 2008/0076808 A1 | 3/2008 | Fray et al. | | |
| 2013/0059057 A1 * | 3/2013 | Mizuuchi | A23K 20/30 | 426/601 |

FOREIGN PATENT DOCUMENTS

| | | |
|---|---|---|
| EP | 0 003 407 A1 | 8/1979 |
| EP | 1 951 067 B1 | 7/2017 |
| RU | 2 350 124 C2 | 3/2009 |
| WO | WO 98/56263 A1 | 12/1998 |
| WO | WO 99/48384 A2 | 9/1999 |
| WO | WO 01/17365 A1 | 3/2001 |
| WO | WO 02/07531 A1 | 1/2002 |

OTHER PUBLICATIONS

Marsh et al., “Effects of zinc and linoleic acid supplementation on the skin and coat quality of dogs receiving a complete and balanced diet,” Veterinary Dermatology, 11(4):277-284 (2000).

Supplementary European Search Report dated Jun. 30, 2022 in Application No. EP 19860150.

Bajwa, “Canine Malassezia Dermatitis”, The Canadian Veterinary Journal, 58(10):1119-1121 (2017).

Campbell, “Fatty Acid Supplementation and Skin Disease”, Veterinary Clinics of North America: Small Animal Practice, vol. 20(6):1475-1486 (1990).

Du Plessis, et al., “International guidelines for the in vivo assessment of skin properties in non-clinical settings: Part 2. transepidermal water loss and skin hydration”, Skin Research and Technology, 19:265-278 (2013).

International Search Report dated Nov. 27, 2019 in International Application No. PCT/US2019/050398.

Watson et al., “Dietary constituents are able to play a beneficial role in canine epidermal barrier function”, Experimental Dermatology, 15:74-81 (2006).

Watson, “Diet and Skin Disease in Dogs and Cats”, Nutrition and Disease, American Society for Nutritional Sciences, vol. 128(12):2783S-2789S (1998).

Finke, “Evaluation of the Energy Requirements of Adult Kennel Dogs,” J. Nutr. 121:S22-S28 (1991).

* cited by examiner

*Primary Examiner* — Robert S Cabral
(74) *Attorney, Agent, or Firm* — Baker Botts L.L.P.

(57) ABSTRACT

The present invention relates to the use of a diet or foodstuff comprising linoleic acid in an amount ranging from 7 g/Mcal to 9 g/Mcal for sustaining or improving skin quality of a healthy pet. In some embodiments, the diet or foodstuff further comprises zinc in an amount of about 50 mg/Mcal. It further pertains to a diet or foodstuff comprising linoleic acid in an amount ranging from 7 g/Mcal to 9 g/Mcal for use in a method for treating a pet animal affected with a skin disorder or disease.

13 Claims, 1 Drawing Sheet

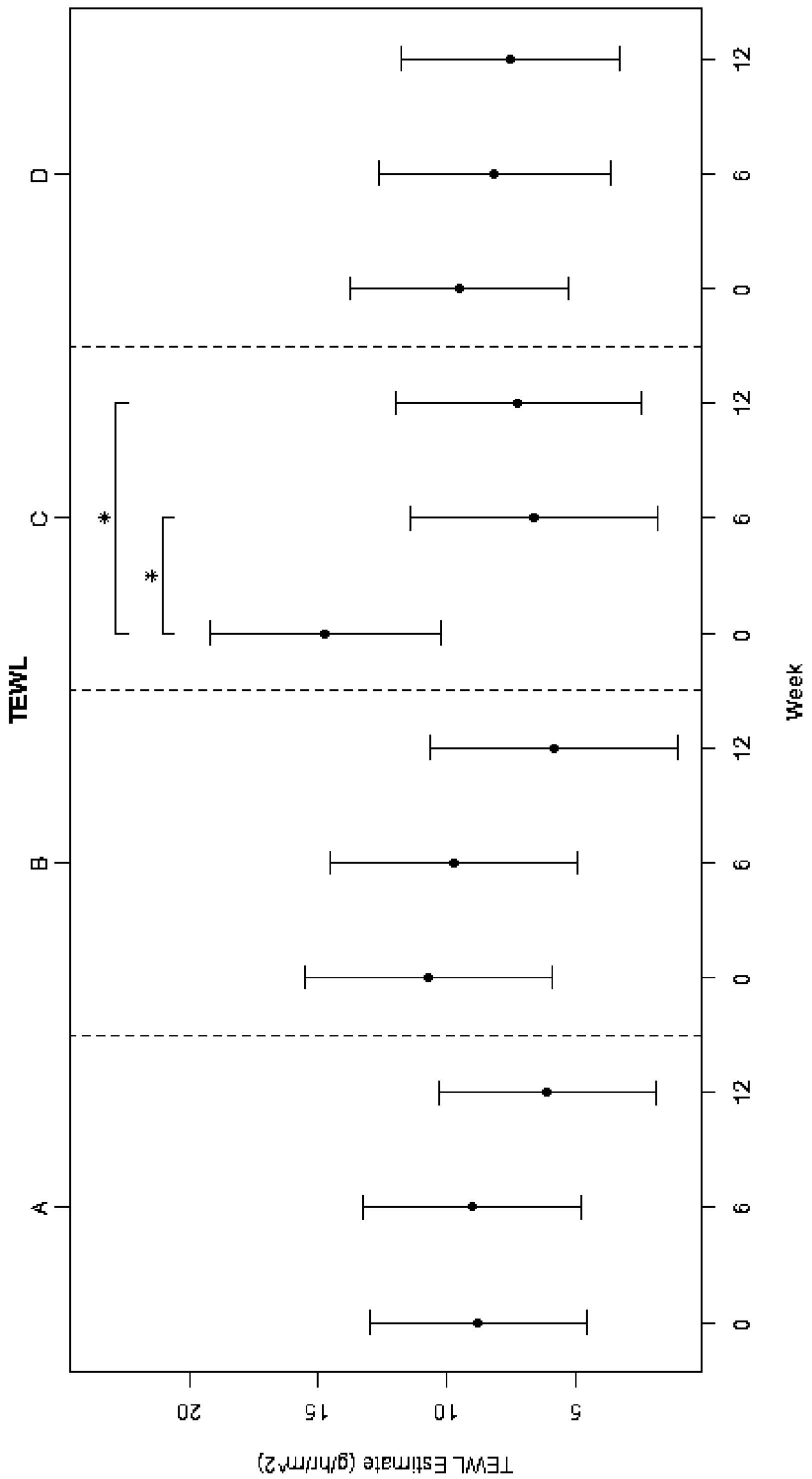
TEWL
TEWL Estimate (g/h/m^2)
Week
A
B
C
D
0
6
12
5
10
15
20
*
*

COMPOSITIONS CONTAINING LINOLEIC ACID

CROSS-REFERENCE TO RELATED APPLICATIONS

This application is a U.S. National Stage Patent Application under 35 U.S.C. § 371 of International Patent Application No. PCT/US2019/050398, filed on Sep. 10, 2019, which claims the benefit of priority to European Patent Application Serial No. EP18306184.5 filed on Sep. 10, 2018, the contents of each of which are hereby incorporated by reference in their entireties, and to each of which priority is claimed.

FIELD OF THE INVENTION

The present disclosure relates to the field of compositions comprising linoleic acid for improving skin quality of healthy pet animals or for treating pet animals affected with a disease causing a skin or dermatological disorder.

BACKGROUND OF THE INVENTION

Skin-associated issues are among the most commonly experienced by dogs and cats, causing great anxiety and resulting in considerable time and effort being expended in order to resolve. This is why maintaining the pet skin in an optimal condition may be viewed as a goal to reach by pet owners. As the skin and coat condition of a pet provides an important visual impact, it is of considerable interest to deliver visible enhancements in animals with already healthy skin and coat condition. The skin of pets, including the skin of dogs, is thin as compared with humans, making them susceptible to skin complaints. Thus, enhancing skin condition is good for the pets, since skin helps protect against dehydration and environmental temperature changes.

The health of the skin and coat, and thus the visual appearance of the pet coat, may be compromised during times of nutritional deficiencies.

It is known in the art that dietary factors have a major role in the maintenance of healthy coat and skin of animal pets. Levels of nutrients in pet foods are well documented as to the provision of a complete and balanced food for healthy animals. For example, dietary zinc is considered as an important element involved in healthy development of coat and skin. The presence of zinc is of particular importance in the rapidly-dividing epidermis (Watson, 1998, J Nutr, Vol. 128 (12 Suppl): 27835-27895). Linoleic acid is also important for skin and coat condition. Notably, dogs are unable to synthesize this fatty acid so a dietary source is essential. Fatty acids are important for maintaining cell membrane fluidity and the cutaneous water permeability water barrier (Campbell, 1990, Vet Clin North Am Anim Pract., Vol. 29 (6): 1373-1383). A wide range of other nutrients, including B vitamins, also have a role in the skin condition (Watson et al., 2006, Exp Dermatol, Vol. 15 (1): 74-81).

It has been shown in the art that improving skin and coat condition might be obtained by providing diets comprising amounts of linoleic acid and zinc in amounts above the amounts thereof that are found in conventional pet foods. Noticeably, the U.S. Pat. No. 6,331,567 discloses a foodstuff for improving pet skin condition, comprising a combination of zinc and linoleic acid. This prior art document discloses tests of skin and coat condition of dogs to which control and test diets comprised (i) 1.8 g/400 kcal or 6 g/kcal of linoleic acid and (ii) 12.5 mg/400 kcal or 40 mg/400 kcal of zinc, respectively. As compared with the control diet, a significant increase in coat gloss and improvement in skin scale was observed with the test diet. With the test diet, a decrease of the epidermal water loss of the dogs' skin was also determined. A decrease in the epidermal water loss was also obtained with a diet exclusively supplemented with zinc, thus in the absence of supplemental linoleic acid. Excellent enhancement of skin and coat condition properties were also obtained with diets comprising a lower amount of zinc, namely diets comprising 6 g/kcal of linoleic acid and 25 mg/400 kcal of zinc.

There remains a need in the art for pet diets, including for dog diets, allowing sustaining or improving skin condition of healthy pet animals.

As previously stated, in most household pets, a healthy skin and coat indicates an animal in general good health.

However, pet animals may in some occasions be affected with dermatological disorders. Thus, it is also an ongoing aim in the art to improve the skin and hair conditions of pet animals, in particular where the pet animal suffers from a skin disorder.

Illustratively, canine skin disease is the single most common reason for a pet to be taken to a veterinary practice. It is suggested that the proportion of animals suffering from such diseases account for in the order of 15% of the workload of such practices. The main conditions which contribute to this statistic are flea allergic dermatitis, atopic (allergic) dermatitis, pyoderma (bacterial infection), seborrhea and mange (demodectic and sarcoptic). In the majority of these skin diseases, the barrier properties of the skin are substantially compromised leading, among others, to an altered trans-epidermal water loss.

Thus, in a distinct aspect, there is also a need in the art for pet compositions enabling treatment of pet animals affected with a skin disorder or disease.

SUMMARY OF THE INVENTION

The present disclosure relates to the use of a diet or foodstuff comprising linoleic acid in an amount ranging from about 7 g/Mcal to about 9 g/Mcal for sustaining or improving skin quality of a pet. In some embodiments, the diet or foodstuff comprises linoleic acid in an amount ranging from 7 g/Mcal to 9 g/Mcal.

In some embodiments, linoleic acid is present in an amount of about 8 g/Mcal, e.g., in an amount of 8 g/Mcal.

In some embodiments, the diet or foodstuff comprises one or more sources of linoleic acid selected for example in the group consisting of safflower oil, sunflower oil, soybean oil, sesame oil, canola oil, meats, and a combination of two or more thereof.

In some embodiments, the diet or foodstuff further comprises zinc in an amount ranging from about 40 mg/Mcal to about 60 mg/Mcal, e.g., in an amount ranging from 40 mg/Mcal to 60 mg/Mcal. In particular embodiments, the diet or foodstuff further comprises zinc in an amount of about 50 mg/Mcal, e.g., in an amount of 50 mg/Mcal.

In some embodiments, the diet or foodstuff comprises one or more sources of zinc selected for example in the group consisting of zinc sulphate, zinc oxide, organic zinc complexes such as chelated zinc, zinc orotate, zinc picolinate, zinc gluconate, zinc acetate, and a combination of two or more thereof.

In some embodiments, the pet is a dog.

This disclosure also relates to a method for sustaining or improving skin quality of a pet animal, especially of a dog, comprising a step of feeding the pet animal with a diet or foodstuff as described in the present disclosure.

The present disclosure also pertains to a diet or foodstuff comprising linoleic acid in an amount ranging from about 7 g/Mcal to about 9 g/Mcal for sustaining or improving skin quality of a pet animal. In some embodiments, the diet or foodstuff comprises linoleic acid in an amount ranging from 7 g/Mcal to 9 g/Mcal. In some embodiments, the diet or foodstuff comprises linoleic acid in an amount of about 8 g/Mcal, e.g., in an amount of 8 g/Mcal.

In some embodiments, the diet or foodstuff further comprises zinc in an amount ranging from about 40 mg/Mcal to about 60 mg/Mcal, e.g., from 40 mg/Mcal to 60 mg/Mcal. In particular embodiments, the diet or foodstuff further comprises zinc in an amount of about 50 mg/Mcal, e.g., in an amount of 50 mg/Mcal.

In some embodiments, the diet or foodstuff is a diet or foodstuff for dogs.

The present disclosure also concerns a diet or foodstuff comprising linoleic acid in an amount ranging from about 7 g/Mcal to about 9 g/Mcal for use in a method for treating a pet animal affected with a skin disorder or disease. In some embodiments, the diet or foodstuff comprises linoleic acid in an amount ranging from 7 g/Mcal to 9 g/Mcal for use in a method for treating a pet animal affected with a skin disorder or disease.

The present disclosure also relates to the use of linoleic acid in an amount ranging from about 7 g/Mcal to about 9 g/Mcal, e.g., from 7 g/Mcal to 9 g/Mcal, for preparing a medicinal diet or foodstuff for treating dogs affected with a skin disorder or disease.

The present disclosure also relates to a method of sustaining or improving skin quality of a healthy pet animal, the method including feeding to the healthy pet animal a diet or foodstuff including linoleic acid in an amount ranging from about 7 g/Mcal to about 9 g/Mcal, e.g., from 7 g/Mcal to 9 g/Mcal.

In some embodiments, linoleic acid is present in an amount of about 8 g/Mcal, e.g., in an amount of 8 g/Mcal. In some embodiments, the diet or foodstuff includes one or more sources of linoleic acid selected from the group consisting of safflower oil, sunflower oil, soybean oil, sesame oil, canola oil, meats, and a combination of two or more thereof.

In some embodiments, the diet or foodstuff further includes zinc in an amount ranging from about 40 mg/Mcal to about 60 mg/Mcal, e.g., from 40 mg/Mcal to 60 mg/Mcal. In some embodiments, the diet or foodstuff further includes zinc in an amount of about 50 mg/Mcal, e.g., in an amount of 50 mg/Mcal. In some embodiments, the diet or foodstuff includes one or more sources of zinc selected from the group consisting of zinc sulphate, zinc oxide, organic zinc complexes such as chelated zinc, zinc orotate, zinc picolinate, zinc gluconate, zinc acetate, and a combination of two or more thereof.

In certain embodiments, trans-epidermal water loss (TEWL) is decreased in the healthy pet animal. In particular embodiments, the healthy pet animal is a healthy dog.

The present disclosure further describes a method of treating a skin disorder or disease in a pet animal in need thereof, the method including feeding to the pet animal a diet or foodstuff including linoleic acid in an amount ranging from about 7 g/Mcal to about 9 g/Mcal, e.g., from 7 g/Mcal to 9 g/Mcal. In some embodiments, the skin disorder or disease is selected from the group consisting of dermatitis, psoriasis, atopic dermatitis, cutaneous form of food allergy, pruritic diseases, bacterial folliculitis, and furunculosis.

In some embodiments, linoleic acid is present in an amount of about 8 g/Mcal, e.g., in an amount of 8 g/Mcal. In some embodiments, the diet or foodstuff includes one or more sources of linoleic acid selected in the group consisting of safflower oil, sunflower oil, soybean oil, sesame oil, canola oil, meats or a combination of two or more thereof.

In some embodiments, the diet or foodstuff further includes zinc in an amount ranging from about 40 mg/Mcal to about 60 mg/Mcal, e.g., from 40 mg/Mcal to 60 mg/Mcal. In certain embodiments, the diet or foodstuff further includes zinc in an amount of about 50 mg/Mcal, e.g., in an amount of 50 mg/Mcal. In some embodiments, the diet or foodstuff includes one or more sources of zinc selected in the group consisting of zinc sulphate, zinc oxide, organic zinc complexes such as chelated zinc, zinc orotate, zinc picolinate, zinc gluconate, zinc acetate or a combination of two or more thereof.

In certain embodiments, TEWL is decreased in the pet animal. In particular embodiments, the pet animal is a dog.

The foregoing has outlined broadly the features and technical advantages of the present application in order that the detailed description that follows may be better understood. Additional features and advantages of the application will be described hereinafter which form the subject of the claims of the application. It should be appreciated by those skilled in the art that the conception and specific embodiments disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to the organization and method of operation, together with further objects and advantages, will be better understood from the following description.

BRIEF DESCRIPTION OF THE DRAWINGS

FIG. 1 illustrates the results of measuring the trans-epidermal water loss (TEWL) of dogs fed different types of foods. Ordinate: TEWL, as expressed in $g/hr/m^2$. Abscissa: (A) dogs fed with diet A; (B) dogs fed with diet B; (C) dogs fed with diet C; (D) dogs fed with diet D. For each of panels A, B, C and D, time point following starting feeding the dogs with the specified diet, as expressed in week.

DETAILED DESCRIPTION OF THE INVENTION

The inventors have shown that optimal improvement of skin health of a healthy pet animal, notably of a healthy dog, may be obtained by providing the healthy pet animal with a diet or foodstuff comprising linoleic acid in a specific amount range. More precisely, the present inventors have found that an improved skin quality of a healthy pet animal, namely a decreased trans-epidermal water loss (TEWL), was obtained by providing to the healthy pet animal, notably a healthy dog, linoleic acid at the specific amount range.

Incidentally, improvement of skin quality may, in certain circumstances, lead to beneficial effects on body coat, such as on gloss, smoothness and softness of the body coat.

As it is widely known in the art, trans-epidermal water loss (TEWL) is defined as the volume of water that passes from inside to outside of the body through the epidermal layer (see for example du Plessis J, Stefaniak A, Eloff F, John S, Agner T, Chou T C, Nixon R, Steiner M, Franken A, Kudla I, Holness L. International guidelines for the in vivo assessment of skin properties in non-clinical settings: Part 2. Transepidermal water loss and skin hydration. Skin Res Technol. 2013 August; 19(3):265-78).

The present disclosure relates to a diet or foodstuff, especially a diet or foodstuff for a healthy pet animal, comprising linoleic acid in an amount ranging from 7 g/Mcal to 9 g/Mcal. It also relates to the use of a diet or foodstuff comprising linoleic acid in an amount ranging from 7 g/Mcal to 9 g/Mcal for sustaining or improving skin quality of a healthy pet animal, especially for sustaining or improving skin quality of the healthy pet animal.

As used herein, the terms "diet" or "foodstuff" designate a material containing protein, carbohydrate and/or fat, which is used in the body of an organism to sustain growth, repair and vital processes and to furnish energy. Foods may also contain supplementary substances or additives, for example, minerals, vitamins and condiments (See Merriam-Webster's Collegiate Dictionary, 10th Edition, 1993). In a preferred embodiment, a diet or foodstuff according to the present disclosure consists of a nutritionally complete diet or foodstuff that provides the complete and balanced nutritional requirements to the pet animal. Thus, a diet or foodstuff as described herein is a complete pet animal food; e.g., a complete dog food, that is a nutritionally adequate feed with which the pet animal, e.g., the dog, can be fed as the sole ration and is capable of sustaining life without additional food (except water).

The diet or foodstuff may contain a carrier, a diluent, or an excipient. Depending on the intended use, the carrier, diluent, or excipient may be chosen to be suitable for animal use, especially for pet animals use such as dogs and cats.

As used herein, a "pet animal" consists of a pet mammal. Pet mammals encompass dogs, cats, rabbits, hamsters, guinea pigs, rats and mice. Preferred pet animals herein are dogs and cats.

As used herein, "sustaining skin quality" means maintaining skin quality at a substantially stable level with time, e.g., maintaining trans-epidermal water loss level at a substantially stable level with time.

As used herein, "improving skin quality" means achieving a measurable improvement of skin quality, e.g., achieving a measurable decrease in trans-epidermal water loss. The term "skin quality" may refer to skin properties such as skin hydration, skin texture, skin elasticity, skin integrity, skin barrier. A person of skill in the art will select the known methods of measuring the improvement of skin quality (e.g., methods described in the Examples). Illustratively, improvement of skin condition or skin quality may be assessed by measuring a decrease in the trans-epidermal water loss (TEWL), as shown in the examples herein.

For assessing improvement of skin quality of test diets or foodstuffs, a plurality of healthy animal cohorts have been fed with distinct diets or foodstuffs, each diet or foodstuff comprising a given amount of linoleic acid, and then skin quality (e.g., TEWL) was measured (i) at the starting time before feeding with a given foodstuff and (ii) at successive time intervals during the feeding period with the given foodstuff. The experimental results have shown that a substantial improvement of skin quality (e.g., a substantial decrease in TEWL) is obtained with a foodstuff comprising linoleic acid in an amount ranging from about 7 g/Mcal to about 9 g/Mcal, e.g., from 7 g/Mcal to 9 g/Mcal. Further, by comparing the tested distinct foodstuffs, one with each other, it has been found that the most effective foodstuff, for which a significant improvement of skin quality has been measured, is a foodstuff comprising linoleic acid in an amount ranging from about 7 g/Mcal to about 9 g/Mcal, e.g., from 7 g/Mcal to 9 g/Mcal.

As used herein, the expression "x g/Mcal" for a given substance comprised in a diet or foodstuff means that the substance is comprised in an amount of x grams per Mcal contained in the diet of foodstuff.

The inventors' results have also shown that a diet or foodstuff comprising 10 g/Mcal linoleic acid or more does not provide any measurable improvement in skin quality, in particular does not provide any significant decrease in trans-epidermal water loss (TEWL). These latter findings are all the more surprising that prior art such that disclosed in the U.S. Pat. No. 6,331,567 taught that skin condition was improved by diets of foodstuffs comprising at least 4 g/400 kcal linoleic acid (i.e., at least 10 g/Mcal linoleic acid), such as 7 g/400 kcal (i.e., 17.5 g/Mcal).

It has also been found herein that a diet or foodstuff comprising 6 g/Mcal linoleic acid or less does not provide any significant improvement in skin quality, in particular does not provide any significant decrease in trans-epidermal water loss (TEWL).

In some embodiments, the diet or foodstuff comprises about 8 g/Mcal of linoleic acid. In some embodiments, the diet or foodstuff comprises 8 g/Mcal of linoleic acid.

In a diet or foodstuff described herein, linoleic acid may be present in variable amounts in a plurality of substances comprised therein. However, in preferred embodiments, the diet or foodstuff comprises one or more substances wherein linoleic acid is present in a rather high amount. Thus, in some embodiments, the diet or foodstuff described herein comprises one or more substances which are sources of linoleic acid, i.e., linoleic acid-containing substances.

Preferred linoleic acid sources, i.e., linoleic acid-containing substances, are preferably vegetable oils, although animal oils or fats may also be used. Preferred linoleic sources, i.e., linoleic acid-containing substances, include safflower oil, sunflower oil, soybean oil, sesame oil, canola oil, other plant or animal oils/fats, meats or a combination of two or more thereof.

Most preferably, linoleic acid sources, i.e., linoleic acid-containing substances, that are comprised in a diet or foodstuff described herein are selected in a group comprising safflower oil, sunflower oil, soybean oil or a combination of two or more thereof.

In some preferred embodiments the diet or foodstuff further comprises zinc.

In a diet or foodstuff described herein, zinc may be present in variable amounts in a plurality of substances comprised therein. However, in preferred embodiments, the diet or foodstuff further comprises one or more substances wherein zinc is present in a high amount, e.g., under the form of zinc salt or zinc complexes.

As shown in the examples, diets or foodstuffs as disclosed herein, which comprise a specified amount of linoleic acid and further an amount of zinc. The zinc can be present in an amount of from about 40 mg/Mcal to about 60 mg/Mcal, e.g., from 40 mg/Mcal to 60 mg/Mcal. In some embodiments, the zinc is present in an amount of about 50 mg/Mcal, e.g., in an amount of 50 mg/Mcal. A diet or foodstuff disclosed herein comprising a specific amount of linoleic acid and further an amount of zinc, e.g., in the amounts disclosed herein, can provide a measurable improvement of skin quality, e.g., a significant decrease of TEWL.

In some embodiments, a diet or foodstuff as described herein comprises both linoleic acid and zinc, at amounts higher than the amounts that are comprised in conventional diets or foodstuffs for pet animals, especially diets or foodstuffs for dogs or cats, and particularly diets of foodstuffs for dogs. Thus, in some embodiments, a diet of foodstuff as described herein comprises (i) linoleic acid at an amount ranging from about 7 g/Mcal to about 9 g/Mcal and (ii) zinc at an amount of about 50 mg/Mcal. In some embodiments, a diet of foodstuff as described herein comprises (i) linoleic acid at an amount ranging from 7 g/Mcal to 9 g/Mcal and (ii) zinc at an amount of about 50 mg/Mcal.

As used herein, a zinc amount of "about 50 mg/Mcal" encompasses an amount of zinc ranging from 45 mg/Mcal to 55 mg/Mcal, which includes ranging from 48 mg/Mcal to 52 mg/Mcal. In some embodiments, zinc is present in an amount of 50 mg/Mcal.

In some embodiments, the diet or foodstuff comprises (i) linoleic acid at an amount ranging from about 7 g/Mcal to about 9 g/Mcal and (ii) zinc in an amount ranging from 40 mg/Mcal to 60 mg/Mcal, e.g., from 45 mg/Mcal to 55 mg/Mcal, e.g., 50 mg/Mcal. In some embodiments, the diet or foodstuff comprises (i) linoleic acid at an amount ranging from 7 g/Mcal to 9 g/Mcal and (ii) zinc in an amount ranging from 40 mg/Mcal to 60 mg/Mcal, e.g., from 45 mg/Mcal to 55 mg/Mcal, e.g., 50 mg/Mcal.

In some preferred embodiments, zinc sources, i.e., zinc-containing substances, encompass zinc sulphate, zinc oxide, organic zinc complexes such as chelated zinc, zinc orotate, zinc picolinate, zinc gluconate, zinc acetate or a combination of two or more there. In some preferred embodiments, zinc sources, i.e., zinc-containing substances, are selected in a group comprising zinc sulphate, zinc oxide, organic zinc complexes or a combination of two or more thereof.

According to the present disclosure, the concentrations of linoleic acid and zinc, when these substances are combined in a diet or foodstuff as described herein, may be used in any concentration, i.e., (i) any concentration of linoleic acid in the range from about 7 g/Mcal to about 9 g/Mcal, e.g., from 7 g/Mcal to 9 g/Mcal, or in an amount of 8 g/MCal, with (ii) any concentration of about 50 mg/Mcal, such as any concentration of zinc in the range from about 40 mg/Mcal to about 58 mg/Mcal, e.g., any concentration of zinc in the range from about 45 mg/Mcal to about 55 mg/Mcal, e.g., any concentration of zinc in the range from about 48 mg/Mcal to about 52 mg/Mcal, e.g., any concentration of zinc in the range from 40 mg/Mcal to 58 mg/Mcal, e.g., any concentration of zinc in the range from 45 mg/Mcal to 55 mg/Mcal, e.g., any concentration of zinc in the range from 48 mg/Mcal to 52 mg/Mcal. Such concentrations encompass about 8 g/Mcal linoleic acid and about 50 mg/Mcal zinc. Such concentrations also encompass 8 g/Mcal linoleic acid and 50 mg/Mcal zinc.

Since zinc and linoleic acid are ubiquitous in food, it will usually be necessary to determine the concentration of each which is present in the ingredients of the diet or foodstuff and then add sufficient quantities to bring the total concentration of each up to the required levels, according to the present disclosure. Illustratively, a required amount of linoleic acid or linoleic-containing substance may be added to a conventional pet diet or foodstuff which already comprises linoleic acid, but in an amount lower than the required amount. Yet illustratively, a required amount of one or more zinc-containing substances may be added to a conventional pet diet or foodstuff which already comprises zinc, but in an amount lower than the required amount.

For measuring the content of a food composition in linoleic acid, the one skilled in the art may refer to any of well-known techniques. As an example, it can be used for dry or wet diets a method based upon the norm NF EN ISO 5508/5509 via chromatography in gaseous phase.

For measuring the content of a food composition in zinc, the one skilled in the art may refer to any of well-known techniques. As an example, it can be used a method based upon the norm NF EN ISO 6869 via spectrometry by atomic absorption or via ICP (for wet diet).

As already specified previously in the present disclosure, the diet or foodstuff described herein most preferably consists of a complete and balanced food (for example, as described in National Research Council, 1985, Nutritional Requirements for Dogs, National Academy Press, Washington D.C., or Association of American Feed Control Officials, Official Publication 1996, the disclosure of each of which is incorporated by reference herein). That is, the concentration levels of zinc and linoleic acid specified herein preferably are used with a high-quality commercial food. As used herein, "high-quality commercial food" refers to a diet manufactured to produce the digestibility of the protein of 80% or more, as set forth in, for example, the recommendations of the National Research Council above for dogs. Similar high nutrient standards would be used for other animals and humans.

A diet or foodstuff as described herein consists of a non-human animal diet or foodstuff which is a wet or dry composition (food). Wet food usually describes food which is sold in tins- and has a moisture content of 70% to 90%. Dry food usually describes food which is of a similar composition, but with 5% to 15% moisture and therefore is presented as small biscuit-like kibbles.

In preferred embodiments, the diet or foodstuff described herein consists of a diet or a foodstuff for dogs.

The diet or foodstuff can be made according to any method known in the art such as, for example, that described in Waltham Book of Dog and Cat Nutrition, Ed. ATB Edney, Chapter by A. Rainbird, entitled "A Balanced Diet" in pages 57 to 74, Pergamon Press Oxford, the disclosure of which is incorporated by reference herein. The concentrations of zinc and linoleic acid to be added to the diet/foodstuff are calculated on the basis of the energy content of the diet/foodstuff and of any additional nutrients which may be consumed by the animal.

The present description includes a method for preparing the diet or foodstuff specified herein. The process for the manufacture of the foodstuffs as described can be made according to any method known in the art.

The diet or foodstuff may be manufactured by mixing together ingredients and kneading in order to make consistent dough or meat emulsion that can be cooked. This applies also to liquids where ingredients are mixed, homogenized before a cooking step in a packaging. The process of creating an embodiment of a dry pet food is usually done by baking and/or extruding. The dough is typically fed into a machine called an expander and/or extruder, which uses pressurized steam or water to cook the ingredients. While inside the extruder, the dough is under extreme pressure and high temperatures. The dough is then pushed through a die (having a specifically sized and shaped hole) and then cut off using a knife. The puffed dough pieces are made into kibble by passing it through a dryer so that moisture is dropped down to a defined target ensuring stability of the food until consumption. The kibble can then be sprayed with fats, oils, minerals, vitamins, the natural extracts cocktail, palatants and optionally sealed into packages.

The composition may be presented as a powder or crumbs, including a white powder or solid form. A powder is useful to be added on the main food of the animal. Other forms include solid pellets, granules, tablets or a liquid.

The diet of foodstuff herein is preferably packaged. In this way, the consumer is able to identify, from the packaging, the ingredients in the food product and confirm that it is suitable for the particular pet in question. The packaging may be metal, plastic, paper or card.

The composition as in the form of a diet or foodstuff can encompass any product which a pet consumes in its diet. Thus, the present disclosure covers standard food products as well as pet food snacks (for example, snack bars, biscuits and sweet products). The diet or foodstuff herein is preferably a cooked product. It may incorporate meat or animal derived material such as a material derived from beef, chicken, turkey, pork, duck, kangaroo, lamb or fish, blood plasma, bone marrow, feather-derived material (e.g., feather hydrolysate such as poultry feather hydrolysate) etc. The product alternatively may be meat free (preferably including a meat substitute such as soya, maize gluten or a soya hydrolysate) in order to provide a protein source. The product may contain additional protein sources such as vegetal protein (wheat gluten, pea protein) or soya protein concentrate or hydrolysate, milk proteins, gluten, etc.). The product may also contain a starch source such as one or more grains (e.g., wheat, corn, rice, oats, barley, etc.), or carbohydrates coming from other sources such as potato or may be starch free. The product may include fiber such as chicory, sugar beet pulp, etc. and/or components such as inulin, fructooligosaccharides, probiotics, most preferably, the combined ingredients of the diet or foodstuff provide all the recommended vitamins and minerals for the particular animal in question (a complete and balanced food) for example as described in National Research Council, 1985, Nutritional Requirements for dogs, National Academy Press, Washington DC or Association of America Feed Control Officials, Official Publication 1996.

As already specified elsewhere herein, a diet of foodstuff of the present disclosure improves skin quality, notably by decreasing trans-epidermal water loss (TEWL), e.g., in a pet animal, such as a dog.

Thus, in some preferred embodiments, the diet or foodstuff is adapted to feeding healthy dogs.

In some preferred embodiments, the diet or foodstuff is used for sustaining or improving skin quality of healthy dogs.

The term "healthy pet animal," as used herein, refers to a pet animal that is not affected with any skin disorder or disease. For instance, the healthy pet animal can be a healthy dog. As used herein, "healthy dogs" consists of dogs which are not affected with any skin disorder or disease. Skin disorders or diseases encompass dermatitis, psoriasis, atopic dermatitis, cutaneous form of food allergy, pruritic diseases, bacterial folliculitis, and furunculosis. Dermatitis encompass allergic dermatitis (such as flea-bite allergic dermatitis or cutaneous adverse food reaction), atopic dermatitis (such as environmental atopy), pyoderma (bacterial infection), mange (demodectic and sarcoptic) and immune or auto-immune dermatitis.

The present disclosure also relates to a method for sustaining or improving skin quality of a healthy pet animal, comprising a step of feeding the healthy pet animal with a diet or foodstuff as described herein.

In some embodiments, the method comprises a step of feeding the healthy pet animal with a diet or foodstuff comprising linoleic acid in an amount ranging from about 7 g/Mcal to about 9 g/Mcal. In some embodiments, the method comprises a step of feeding the healthy pet animal with a diet or foodstuff comprising linoleic acid in an amount ranging from 7 g/Mcal to 9 g/Mcal. In some embodiments, the diet or foodstuff comprises linoleic acid in an amount of about 8 g/Mcal, e.g., 8 g/Mcal.

In some embodiments, the diet or foodstuff further comprises zinc in an amount of about 50 mg/Mcal, such as in an amount ranging from about 40 mg/Mcal to about 60 mg/Mcal, e.g., from about 45 mg/Mcal to about 55 mg/Mcal, e.g., from 40 mg/Mcal to 60 mg/Mcal, e.g., from 45 mg/Mcal to 55 mg/Mcal, e.g., 50 mg/Mcal.

In preferred embodiments of the feeding method, the healthy pet animal, e.g., the healthy pet dog, is fed with the diet or foodstuff described herein on a daily basis. In other embodiments, the healthy pet animal, e.g., the healthy pet dog, is fed with the diet or foodstuff described herein every two, three of four days.

This disclosure also related to a diet or foodstuff comprising linoleic acid in an amount ranging from about 7 g/Mcal to about 9 g/Mcal, e.g., from 7 g/Mcal to 9 g/Mcal, such as in an amount of about 8 g/Mcal, for sustaining or improving skin quality of a pet animal. In some embodiments, the diet or foodstuff comprises linoleic acid in an amount of 8 g/Mcal.

In some embodiments, the diet or foodstuff comprises (i) linoleic acid at an amount ranging from about 7 g/Mcal to about 9 g/Mcal and (ii) zinc in an amount ranging from about 40 mg/Mcal to about 60 mg/Mcal; for sustaining or improving skin quality of a pet animal. In some embodiments, the diet or foodstuff comprises (i) linoleic acid at an amount ranging from 7 g/Mcal to 9 g/Mcal and (ii) zinc in an amount ranging from 40 mg/Mcal to 60 mg/Mcal; for sustaining or improving skin quality of a pet animal.

In some embodiments, the diet or foodstuff further comprises zinc in an amount of about 50 mg/Mcal. In some embodiments, the diet or foodstuff further comprises zinc in an amount of 50 mg/Mcal.

In some embodiments, the diet or foodstuff is a diet or foodstuff for dogs.

The experimental results contained in the examples show that the diet or foodstuff described herein improves skin quality and it is specified that the improvement in skin quality leads to beneficial effects on body coat, such as on gloss, smoothness and softness of the body coat of healthy pet animals, e.g., of healthy dogs.

The present inventors have also determined that the improvement of skin quality that is provided by the diet or foodstuff described herein may also benefit to pet animals affected with a skin disorder or disease. Indeed, skin disorders or diseases cause alterations to the skin barrier, e.g., leading to an altered trans-epidermal water loss, which may be remedied by feeding the non-healthy pet animal with the diet or foodstuff.

Thus, according to a second aspect of the present disclosure, the diet or foodstuff described herein may be used for a therapeutic purpose for treating pet animals affected with a skin disorder or disease.

According to the above second aspect, the present disclosures relates to a diet or foodstuff comprising linoleic acid in an amount ranging from about 7 g/Mcal to about 9 g/Mcal, e.g., from 7 g/Mcal to 9 g/Mcal, for use for treating a pet animal affected with a skin disorder or disease.

In some embodiments, the present disclosure relates to a method of treating a pet animal affected with a skin disorder or disease, the method comprising feeding to the pet animal a diet or foodstuff comprising linoleic acid in an amount ranging from about 7 g/Mcal to about 9 g/Mcal, e.g., from 7 g/Mcal to 9 g/Mcal.

According to this second aspect, the present disclosure further pertains to the use of linoleic acid in an amount ranging from about 7 g/Mcal to about 9 g/Mcal, e.g., from 7 g/Mcal to 9 g/Mcal, for preparing a medicinal diet or foodstuff for treating dogs affected with a disease causing a skin or a dermatological disorder.

Still according to this second aspect, the present disclosure also concerns a method for treating a pet animal affected with a skin disorder or disease comprising feeding the pet animal with a diet or foodstuff comprising linoleic acid in an amount ranging from about 7 g/Mcal to about 9 g/Mcal, e.g., from 7 g/Mcal to 9 g/Mcal.

According to this second aspect, skin disorders or diseases are preferably selected in a group comprising dermatitis, psoriasis, atopic dermatitis, cutaneous form of food allergy, pruritic diseases, bacterial folliculitis, and furunculosis. Dermatitis encompass allergic dermatitis (such as flea-bite allergic dermatitis or cutaneous adverse food reaction), atopic dermatitis (such as environmental atopy), pyoderma (bacterial infection), mange (demodectic and sarcoptic) and immune or auto-immune dermatitis.

For the sake of clarity, in preferred embodiments of the second aspect of the disclosure, the food or diet that is used for a therapeutic purpose on pet animals affected with a skin disorder or disease may be any embodiment of a diet or foodstuff that is described elsewhere in the present disclosure when used for improving the skin quality of a healthy pet animal. Otherwise stated, the various embodiments of a diet of foodstuff that are described elsewhere herein for a non-therapeutic purpose are expressly incorporated as possible embodiments of a diet or foodstuff that are used for a therapeutic purpose on pet animals affected with a skin disorder or disease.

The present disclosure is further illustrated by, without in any way being limited to, the examples below.

EXAMPLES

Example 1: A Specific Combination of Linoleic Acid and Zinc Improves Pet Skin Properties

Aim of the Example

The aim was to investigate the effect of diets containing different concentrations of zinc and linoleic acid on skin properties of black Labradors. The diets contain more zinc and linoleic acid than usual minimums such as recommended by the NRC (National Research Council nutrients requirements of cats and dogs), FEDIAF (Fédération Européenne des industries des aliments pour animaux familiers) and AAFCO (Association of American Feed Control Officials) but less than the levels previously shown to improve skin and coat.

A. Materials and Methods

Four diets were fed during the study. A baseline diet with recommended minimum levels of zinc (21 mg/1000 kcal) and linoleic acid (3.8 g/1000 kcal) was fed to all 34 black Labradors for 12 weeks prior to the trial beginning. Dogs were then randomized to 4 groups with 8 dogs per group. One group continued with the baseline diet (diet A) and the other 3 groups were moved onto diets B, C and D which had zinc and linoleic acid concentrations as shown in Table 1 below.

TABLE 1

| Tested diets | | |
|---|---|---|
| Diet | Zinc (mg/1000kcal) | Linoleic Acid (g/1000kcal) |
| A | 21 | 3.8 |
| B | 50 | 6 |
| C | 50 | 8 |
| D | 50 | 10 |

Some other components for each diet are also described in the following Table 2.

TABLE 2

| Other components of diet | | | | |
|---|---|---|---|---|
| | Diet A | Diet B | Diet C | Diet D |
| Ash % (w/w) | 6.2 | 6.9 | 6.9 | 6.5 |
| Cellulose % (w/w) | 1.8 | 1.6 | 1.5 | 1.6 |
| Fat % (w/w) | 13.3 | 14.4 | 13.8 | 13.2 |
| Protein % (w/w) | 25.4 | 24.8 | 24.4 | 24.2 |
| Arachidonic acid (g/Mcal) | 0.129 | 0.129 | 0.143 | 0.163 |
| EPA/DHA (g/Mcal) | 0.15 | 0.11 | 0.12 | 0.15 |

To assess skin properties, trans-epidermal water loss (TEWL) was measured at 0, 6 and 12 weeks from starting feeding the dogs with each of the specified diet/foodstuff.

TEWL measurements were taken at the end of the pre-feed period, and subsequently following 4, 8 and 12 weeks of the differential feeding period. Five separate measurements were taken at each time point for each dog. The dogs were assessed in a quiet, draft free room with consistent environmental conditions. Measurements were taken using a Cutometer MPA580 fitted with a Tewameter Triple TM 330 T (3 Probes measure TEWL simultaneously) placed 1-2 inches to one side of the lumber spine, first parting the hair coat so as to ensure good contact of the probe with the skin. The lumbar region of the animal provided a good surface for orientation of the 3 probes.

Prior to the start of the study the dogs were conditioned to remain stationary for 1 minute at a time to improve stability of readings. The TEWL was measured twice on all dogs at each time point and, for each measurement, was recorded every second for up to 90 seconds using three probes. Based on the probe manufacturer's literature, the expected profile over the 90 seconds was an increase to a plateau, and this plateau was the TEWL value for that measurement. For the analysis, the first 30 seconds of recording were removed and the remaining (up to) 60 seconds were used as repeats. On a statistical point of view, the TEWL was modeled against Week, Diet and the Week by Diet interaction as fixed effects with a random effects structure of Probe nested in Repeat nested in Week nested in Dog. The same contrasts as described for the other models were applied.

B. Results

The estimated TEWL for each diet in weeks 0, 6 and 12 are shown below with 98.75% confidence intervals (CI). The results are shown in Table 3 hereunder.

TABLE 3

| Estimated TEWL | | | | |
|---|---|---|---|---|
| Response | Week | Diet | Estimate | 98.75% CI |
| TEWL | 0 | A | 8.76 | (4.51, 13.01) |
| TEWL | 6 | A | 9.03 | (4.78, 13.28) |
| TEWL | 12 | A | 6.07 | (1.82, 10.32) |
| TEWL | 0 | B | 10.74 | (5.92, 15.56) |
| TEWL | 6 | B | 9.71 | (4.90, 14.53) |
| TEWL | 12 | B | 5.81 | (0.99, 10.62) |
| TEWL | 0 | C | 14.73 | (10.22, 19.23) |
| TEWL | 6 | C | 6.61 | (1.80, 11.43) |
| TEWL | 12 | C | 7.21 | (2.39, 12.02) |
| TEWL | 0 | D | 9.52 | (5.27, 13.77) |
| TEWL | 6 | D | 8.14 | (3.64, 12.63) |
| TEWL | 12 | D | 7.52 | (3.27, 11.77) |

The between diets differences in the changes from week 0 and between week differences within each diet are shown in Table 4 below and in FIG. 1.

TABLE 4

| TEWL differences between diets | | | | |
|---|---|---|---|---|
| Response | Contrast | Estimate | 98.75% CI | p-value |
| TEWL | (DietB:Week6-Week0)-(DietA:Week6-Week0) | −1.29 | (−9.85, 7.28) | 0.9998 |
| TEWL | (DietB:Week12-Week0)-(DietA:Week12-Week0) | −2.24 | (−10.80, 6.33) | 0.9889 |
| TEWL | (DietC:Week6-Week0)-(DietA:Week6-Week0) | −8.38 | (−16.81, 0.06) | 0.0137 |
| TEWL | (DietC:Week12-Week0)-(DietA:Week12-Week0) | −4.82 | (−13.26, 3.61) | 0.4870 |
| TEWL | (DietD:Week6-Week0)-(DietA:Week6-Week0) | −1.65 | (−9.80, 6.51) | 0.9981 |
| TEWL | (DietD:Week12-Week0)-(DietA:Week12-Week0) | 0.70 | (−7.32, 8.71) | 1.0000 |
| TEWL | DietA:Week6-Week0 | 0.26 | (−5.40, 5.93) | 1.0000 |
| TEWL | DietA:Week12-Week0 | −2.69 | (−8.36, 2.97) | 0.7216 |
| TEWL | DietA:Week12-Week6 | −2.96 | (−8.62, 2.71) | 0.6100 |
| TEWL | DietB:Week6-Week0 | −1.02 | (−7.45, 5.40) | 0.9997 |
| TEWL | DietB:Week12-Week0 | −4.93 | (−11.36, 1.49) | 0.1293 |
| TEWL | DietB:Week12-Week6 | −3.91 | (−10.33, 2.52) | 0.3996 |
| TEWL | DietC:Week6-Week0 | −8.11 | (−14.36, −1.86) | **0.0002** |
| TEWL | DietC:Week12-Week0 | −7.52 | (−13.77, −1.27) | **0.0010** |
| TEWL | DietC:Week12-Week6 | 0.59 | (−5.83, 7.02) | 1.0000 |
| TEWL | DietD:Week6-Week0 | −1.38 | (−7.24, 4.48) | 0.9944 |
| TEWL | DietD:Week12-Week0 | −2.00 | (−7.66, 3.67) | 0.9326 |
| TEWL | DietD:Week12-Week6 | −0.61 | (−6.48, 5.25) | 1.0000 |

The results show that trans-epidermal water loss (TEWL) is very highly significantly decreased when the animals are fed with diet C. None of the other diets tested, and in particular none of diet B (6 mg/Mcal linoleic acid and 50 mg/MCal zinc) and D (10 mg/MCal linoleic acid and 50 mg/MCal zinc) does induce significant changes in trans-epidermal water loss (TEWL).

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods or steps.

Patents, patent applications publications product descriptions, and protocols are cited throughout, the disclosures of which are incorporated herein by reference in their entireties for all purposes.

The invention claimed is:

1. A method of sustaining or improving skin quality of a healthy pet animal, the method comprising feeding to the healthy pet animal a diet or foodstuff comprising:

a) linoleic acid in an amount of about 8 g/Mcal;

b) zinc in an amount of about 50 mg/Mcal;

c) arachidonic acid; and d) EPA/DHA.

2. The method of claim 1, wherein linoleic acid is present in an amount of 8 g/Mcal.

3. The method of claim 1, wherein the diet or foodstuff comprises one or more sources of linoleic acid selected from the group consisting of safflower oil, sunflower oil, soybean oil, sesame oil, canola oil, meats, and a combination of two or more thereof.

4. The method of claim 1, wherein the diet or foodstuff further comprises zinc in an amount of 50 mg/Mcal.

5. The method of claim 1, wherein the diet or foodstuff comprises one or more sources of zinc selected from the group consisting of zinc sulphate, zinc oxide, organic zinc complexes such as chelated zinc, zinc orotate, zinc picolinate, zinc gluconate, zinc acetate, and a combination of two or more thereof.

6. The method of claim 1, wherein the healthy pet animal is a healthy dog.

7. A method of treating a skin disorder or disease in a pet animal in need thereof, the method comprising feeding to the pet animal a diet or foodstuff comprising:

a) linoleic acid in an amount of about 8 g/Mcal;

b) zinc in an amount of about 50 mg/Mcal;

c) arachidonic acid; and d) EPA/DHA.

8. The method of claim 7, wherein the skin disorder or disease is selected from the group consisting of dermatitis, psoriasis, atopic dermatitis, cutaneous form of food allergy, pruritic diseases, bacterial folliculitis, and furunculosis.

9. The method of claim 7, wherein linoleic acid is present in an amount of 8 g/Mcal.

10. The method of claim 7, wherein the diet or foodstuff comprises one or more sources of linoleic acid selected from the group consisting of safflower oil, sunflower oil, soybean oil, sesame oil, canola oil, meats, and a combination of two or more thereof.

11. The method of claim 7, wherein the diet or foodstuff further comprises zinc in an amount of 50 mg/Mcal.

12. The method of claim 7, wherein the diet or foodstuff comprises one or more sources of zinc selected from the group consisting of zinc sulphate, zinc oxide, organic zinc complexes such as chelated zinc, zinc orotate, zinc picolinate, zinc gluconate, zinc acetate, and a combination of two or more thereof.

13. The method of claim 7, wherein the pet animal is a dog.

* * * * *